United States Patent [19]

Doherty et al.

[11] Patent Number: 5,665,909
[45] Date of Patent: Sep. 9, 1997

[54] FREE-FALL, WIRE-GUIDED HYDROGRAPHIC PROFILER

[75] Inventors: Kenneth W. Doherty, Falmouth; John M. Toole, North Falmouth; Robert C. Millard, Waquoit, all of Mass.

[73] Assignee: Woods Hole Oceanographic Institution, Woods Hole, Mass.

[21] Appl. No.: 650,040

[22] Filed: May 17, 1996

[51] Int. Cl.⁶ ........................................... G01N 1/00
[52] U.S. Cl. ................................. 73/170.34; 73/170.29
[58] Field of Search ........................ 73/170.33, 170.34, 73/866.5, 170.29

[56] References Cited

U.S. PATENT DOCUMENTS

| | | | |
|---|---|---|---|
| 3,069,905 | 12/1962 | Erdely | 73/170.33 X |
| 3,656,345 | 4/1972 | Ingram | 73/170.34 |
| 3,834,229 | 9/1974 | White, Jr. | 73/170.34 |
| 3,927,562 | 12/1975 | Hickey, Jr. | 73/170.34 |
| 4,554,826 | 11/1985 | Barry | 73/170.34 |
| 5,046,359 | 9/1991 | Layport | 73/170.34 X |
| 5,209,112 | 5/1993 | McCoy et al. | 73/170.01 |
| 5,283,767 | 2/1994 | McCoy | 73/170.34 X |
| 5,379,267 | 1/1995 | Sparks et al. | 73/170.34 X |
| 5,555,518 | 9/1996 | Whalen et al. | 73/170.34 X |

FOREIGN PATENT DOCUMENTS 961838   1/1975   Canada .

OTHER PUBLICATIONS

A Deep Ocean Suspension System for Stabilizing Near–Surface Sensors; P.D. Scully–Power, IEEE International Conference On Engineering in the Ocean Environment; 1973.

*Primary Examiner*—Elizabeth L. Dougherty
*Attorney, Agent, or Firm*—Hartley Hoskins

[57] ABSTRACT

A frame, freely-falling on a cable or wire, for transporting sensing and sampling equipment at a near constant velocity through a body of water, such as an ocean, lake or river. Said apparatus' downward motion is stopped at or near the end of the cable or wire, and the apparatus is subsequently retrieved by raising the cable or making the frame buoyant.

7 Claims, 3 Drawing Sheets

FREE-FALL, WIRE-GUIDED HYDROGRAPHIC PROFILER

ORIGIN OF INVENTION

The invention described herein was made in a proposal to the National Science Foundation and reduced to practice in National Science Foundation Grant OCE-932067, and is subject to the provisions of Public Law 96-517 (35 USC 202) in which the Contractor has elected to retain title.

BACKGROUND OF THE INVENTION

1. Field of Invention

The present invention relates to techniques for measuring properties of water using one or more sensors and/or samplers moving through the water guided by a wire.

2. Description of the Prior Art

The circulation of water bodies, such as the oceans, lakes and rivers, is driven by variation in density and boundary stresses. The water density in turn is largely determined by its temperature, salinity and other chemical attributes. A number of sensors are used to measure these attributes, among them thermometers and conductivity cells. A pressure sensor is also commonly used to determine the depth of the observations. A suite of such sensors are commonly mounted on a frame and called a profiler. This profiler apparatus, usually together with another apparatus mounted on the same frame for taking several water samples at various depths, is typically lowered from a ship or boat at the water surface to the floor of the body of water—a so-called hydrographic cast. The water samples are analyzed on shipboard or stored for subsequent shoreside chemical analyses. Present combined profiling and sampling systems are capable of capturing up to thirty-six 10-liter samples of water. Water depths can range from a few meters to nearly ten thousand meters.

Sensors generally have a finite response time, meaning that a certain interval of time is required before the sensor equilibrates with the water and a valid measurement can be made. Different sensors have different response times. Typically, it is an exponential convergence to the value. This difficulty is discussed in Horne et al, 1980, and Gregg et al, 1982, among others. In the case of a sensor moving through the water, this response time limits the lineal resolution possible. When the movement of the sensor through the water varies in speed, the sensor response time, and therefore the measurement precision, will vary along the traverse. This difficulty is discussed in Giles et al, 1986. Freely-falling, untethered profilers (for example, Hoyt and Bradley, 1988) obviate the problem of varying sensor speed, but do not generally have adequate ability to take water samples. For this reason, most of the hydrographic casts continue to be made with a sensor and sampler assembly on the end of a line or cable.

Limitations of the existing art include:

sensors moving through the water at varying speed giving rise to varying resolution in the measurement of the water properties, such as temperature, conductivity, chemical species, and depth. This variable speed also limits the ability to digitally filter the data to correct for sensor response mismatches. This is important when calculating derived parameters such as salinity, which is a function of temperature, conductivity and pressure.

sensors connected to a wire and lowered from a boat at the surface which is heaving due to waves do not move through the water at a uniform speed because of the motion of the boat, thereby giving rise to varying resolution in the measurements due to the sampling interval not being uniform vertically. At the 25 Hz sampling rate and 1.5 m per second lowering rate commonly used, the vertical spacing of samples can vary from zero to ten centimeters, whereas a uniform sampling interval is desired. FIG. 2 is an example of a hydrographic cast in which the sampler reversed direction due to the heaving motion of the surface ship even though the winch was paying out wire at a constant speed.

the flow of water past an object moving through it depends on its shape, size, inter-connected conduits and the speed. Depending on the speed at which the object is moving, the flow pattern often varies considerably, particularly with the complex shapes of hydrographic profilers. In some instants, the flow can actually reverse and the profiler will sense its wake rather than the surrounding water. In some cases, water may become entrained around the sensors instead of flushing by them. To reduce this problem, one manufacturer has a pump on their instrument to assure some movement of water past the sensor. Reduction of the variation in the speed of the moving sensor is a major step in obviating these changes and instabilities.

the large size of the sampling profilers currently used has considerable drag. Some packages in current use have a cross-sectional area of as much as 1.2 sq. meters. The weight of the frame in air can be as much as 700 kg, and when the sample bottles are filled as much as 1000 kg. When the lowering rate varies, this gives rise to significant transient loads on the cable which have broken the electrical conductor or conductors in the cable, or parted the cable. The double-armored steel cables with one or three conductors commonly used are about 8 mm in diameter with a safe working load of 3000 kg.

because of the relatively slow free-fall speed of the existing profilers, care must be taken not to pay out wire faster than the fall speed of the profiler, else the wire overrun the package and potentially foul on it.

operations in heavy weather are difficult, if not impossible, because of the large dynamic loads on the profiler, wire, wire terminations, winch and fairlead.

SUMMARY OF THE INVENTION

The proceeding and other shortcomings of the prior art are addressed and overcome by the present invention that provides:

In the first instance, a nearly uniform descent velocity of the sensor and sampling profiler moving along a guide wire or cable is achieved. A comparison of FIG. 2 and FIG. 3 shows a twenty-fold reduction in the speed variations compared to a tethered profiler. Reversals in the direction of profiler movement are eliminated.

In the second instance, with less dynamic load on the profiler, the profiler's frame does not have to be as massive or strong to perform its function.

In the third instance, as a consequence of decoupling the rigid connection between the guiding wire and profiler, a braking or impact mechanism on the lower end of the profiler and/or on top of the wire weight is required to stop the profiler's free-fall at the lower end of the wire. Alternatively the profiler can, at a prescribed depth, be made sufficiently buoyant to stop its descent and/or to cause it to ascend; this can be effected by jettisoning ballast.

The foregoing and additional features and advantages of this invention will become further apparent from the detailed descriptions and accompanying drawings that follow. In the figures and written description, numerals indicate the various features of the invention, like numerals referring to like features throughout both the drawing figures and the written descriptions.

DETAILED DESCRIPTION OF THE PREFERRED EMBODIMENTS

Figure 1:
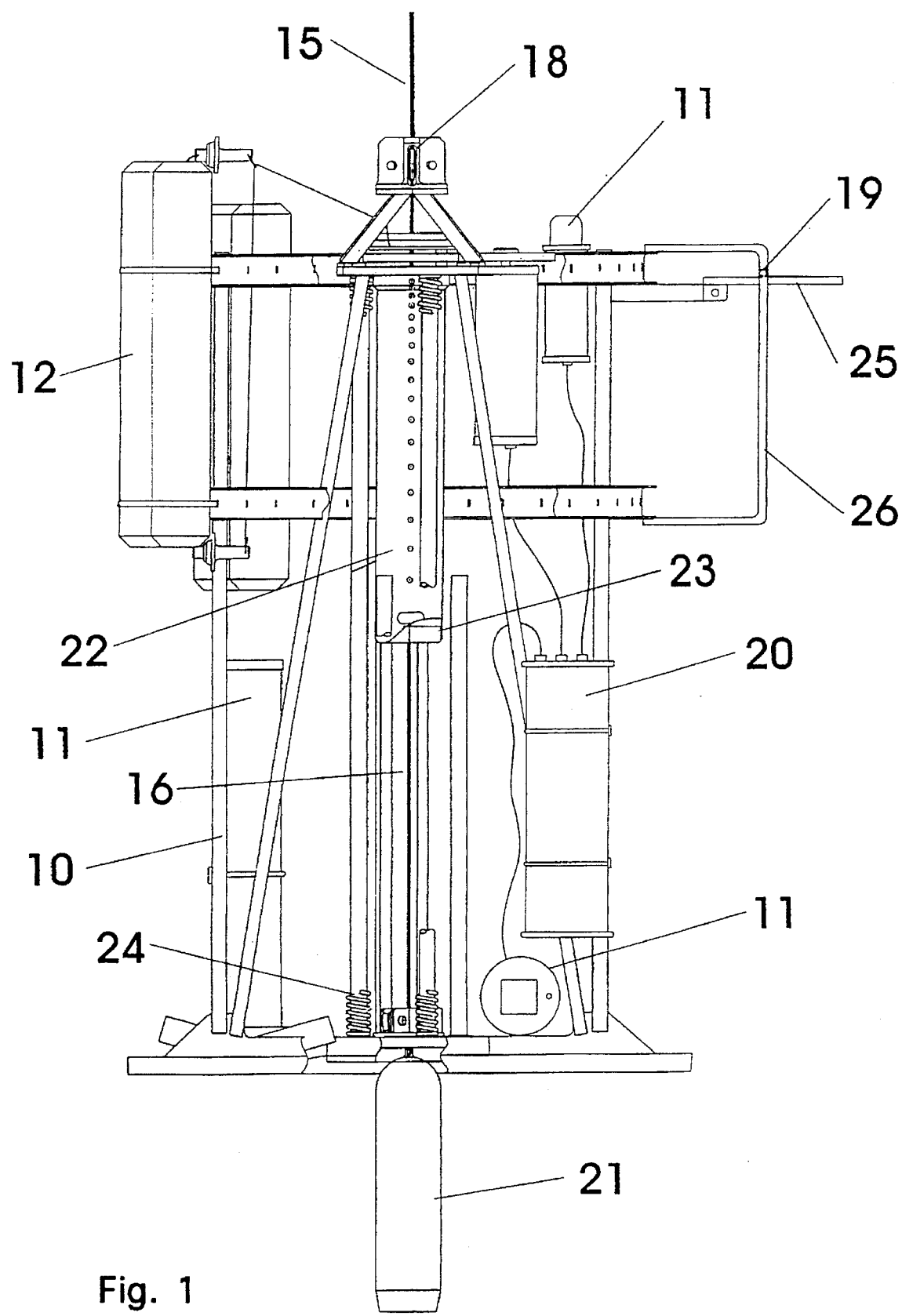
FIG. 1 is a side view of the free-fall hydrographic profiler.
Figure 2:
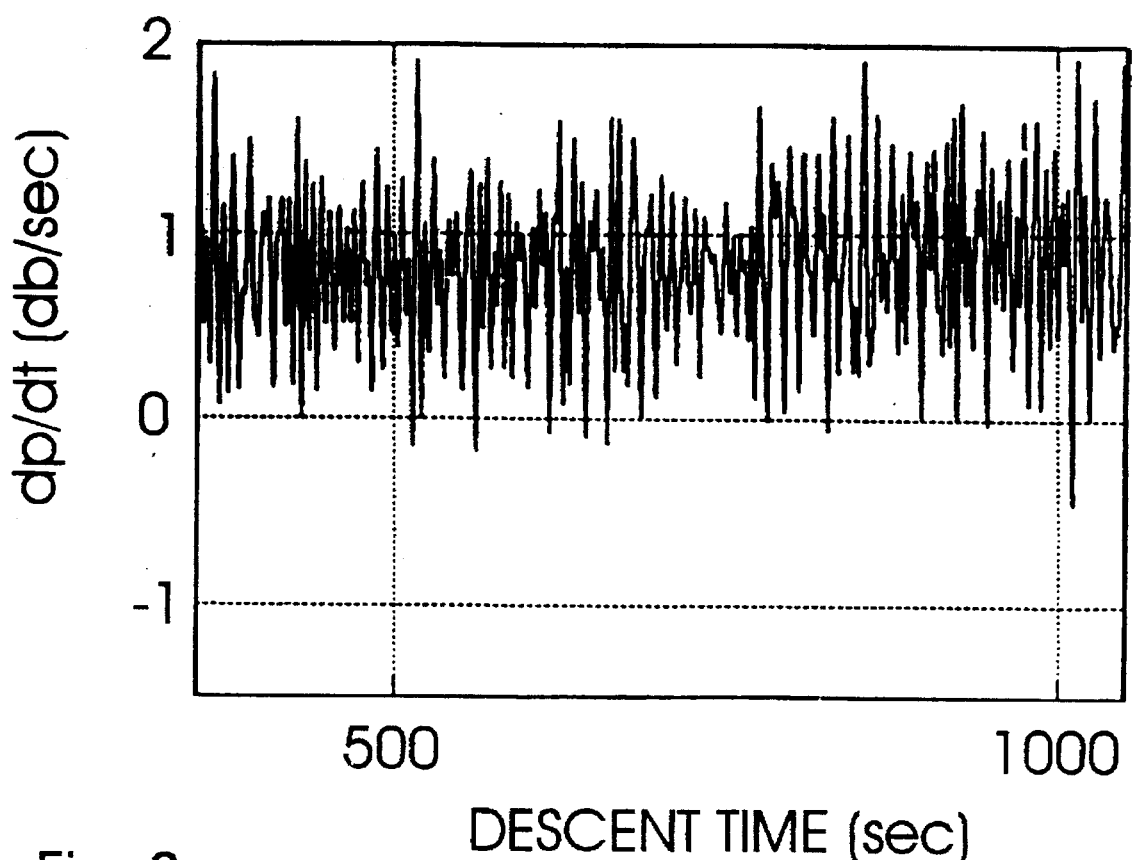
FIG. 2 is a time plot of descent rate of a hydrographic sampling profiler tethered to a wire, the configuration presently in general use. Note that the profiler's speed reverses at several points due to the heaving motion of the ship even though the shipboard winch is paying wire out at a constant speed.
Figure 3:
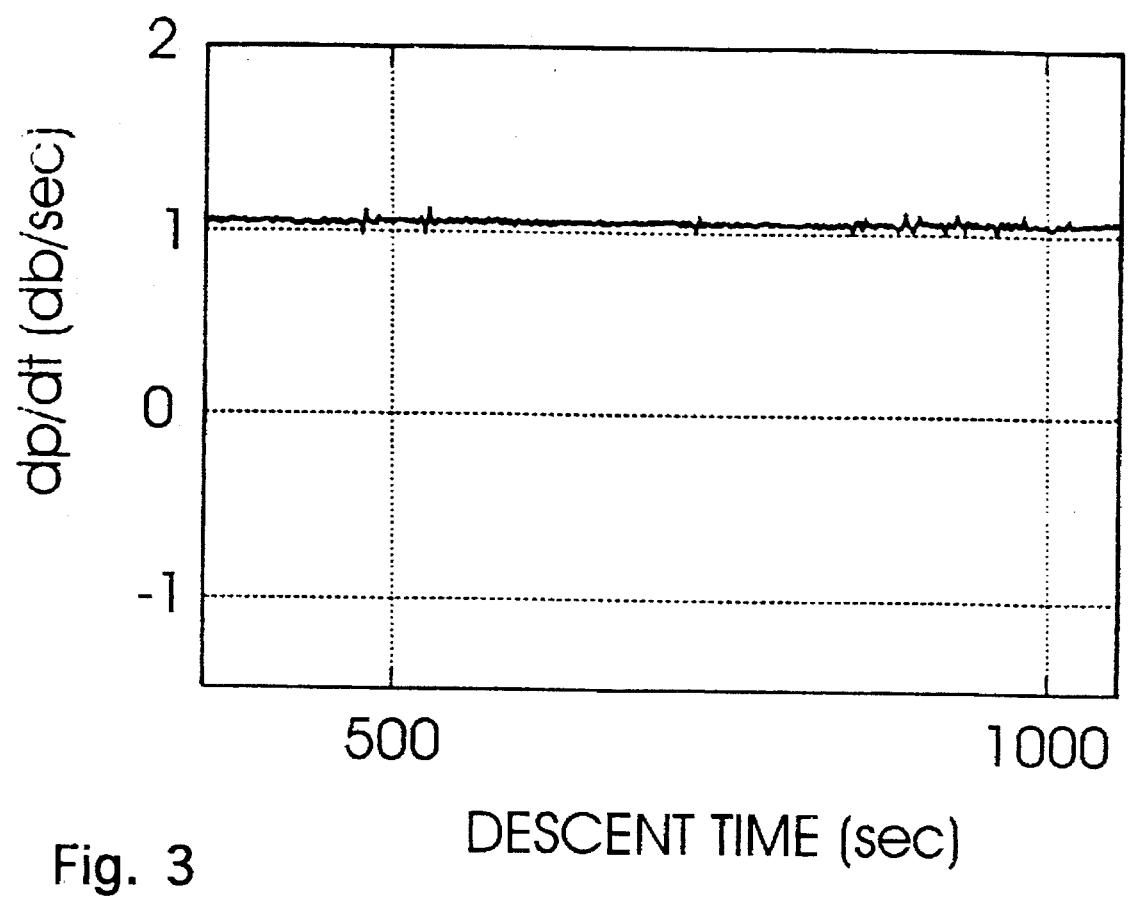
FIG. 3 is a time plot of descent rate of the new free-fall, wire-guided hydrographic profiler. Note that the variation in descent rate is one-twentieth of that shown in FIG. 2, and that there are no speed reversals.

Referring now to FIG. 1 (side view), the profiler apparatus is comprised of frame 10 for holding an instrument or instruments 11 (for example, a thermometer, conductivity cell, acoustic Doppler current profiler), and optionally, one or more fluid samplers 12 (for example, Niskin bottles). The overall shape is configured so that it moves stably in the direction of travel. There is a central passageway or conduit 16 through which a cable 15 passes, allowing the apparatus to slide freely along the cable. The conduit can be a simple through opening, a tube, or may include optional rollers or wire guides 18 near the ends of the opening. An option provides lateral access to the conduit so that the profiler can be attached to and removed from a standing line rather than having to thread the line through the central conduit 16. This can be accomplished by providing a lateral opening sufficient for the cable 15 through the frame 10 with wire guides 18 that open and close.

On a more or less vertical cable, the terminal fall velocity can be field adjusted from 0.2 to over 2 meters per second. For the sensors currently in use, 1.0 to 1.5 m per second is preferred. The terminal descent velocity can be varied by the weight of the components, and the arrangements of the components to vary the overall cross-sectional area in the direction of movement. In some instances it is necessary to add drag elements such as ring 26 on the outside, and/or drag plates 25 mounted perpendicular to the direction of movement to achieve the desired descent velocity. These drag plates can be hinge-mounted 19 so that when the frame is being lifted by the wire, they rotate or hang down offering less drag resistance.

Aluminum, steel, titanium fiberglass and plastics can be used for structural elements and coverings depending on the strength and weight requirements. The components are arranged so that the center of gravity is below the centers of buoyancy and drag and all three are as collinear as feasible with the central conduit 16. Canister 20, usually a pressure housing, contains the control, recording components, and associated power.

One operational consequence of decoupling the frame from the wire is that the wire needs to be lowered faster than the free fall rate of the frame, and/or the wire needs to have been lowered before launching the free. This avoids the profiler overtaking the wire weight 21 at the bottom of the wire.

The frame stops at the end of the cable using an deceleration mechanism. There are two options. One consists of a wire weight 21, a set of springs 24, and conical mating piston 23 and shock absorber cylinder 22. The frame is retrieved by retrieving the wire or cable 15 along which it moved. Another option is to make the frame neutrally-buoyant or positively buoyant at some point in its downward traverse before reaching the wire weight 21, by creating the upward force to make it stop and/or ascend the cable or wire 15. This can be accomplished by dropping ballast from the frame or increasing the buoying displacement.

The size of the apparatus frame 10 is determined by the size and number of instruments carried. The prototype, which carries a temperature sensor, conductivity cell, pressure transducer, acoustic modem, acoustic Doppler current profiler, battery and control module, and thirty-six, 10-liter sample bottles is about 2 m high and 1.2 m in diameter. Depending on the application's equipment requirements, the frame can be larger or smaller, but for each configuration, the overall centers of gravity, buoyancy and drag must be such that the frame moves stably along the wire. This requires the center of gravity to be below that of the centers of buoyancy and drag. In addition to calculating these parameters, some experimentation is generally required to optimize performance.

Another operational consequence of decoupling the frame from the wire is the inability to use a electromechanical cable (a cable with one or more power and/or communications leads in addition to the strength members) to carry real-time data from the profiler up to the ship. Two established alternative techniques that can be used to provide a real-time telemetry link back to the ship are: an acoustic modem, or a modem which inductively couples to the cable (Frye et al., 1990).

What is claimed is:

1. Apparatus for transporting equipment such as sensors and samplers at a near-uniform speed along a cable or wire suspended in a body of water, comprising:

a frame with a central passageway allowing the apparatus to slide along a cable or wire, frame, sensors, and/or samplers arranged so that their collective center of gravity lies below their collective centers of buoyancy and drag and said centers of gravity, buoyancy and drag are approximately collinear with the central passageway, said frame, said sensors, said samplers and optional drag surfaces spatially arranged so that their weight and drag cause the frame to slide along the cable or wire stably at pre-determined rates, means to decelerate and stop the descending frame at the lower end of the wire or cable, whereupon the frame is retrieved by raising the cable or wire.

2. Apparatus for transporting equipment such as sensors and samplers at a near-uniform speed along a cable or wire suspended in a body of water, comprising:

a frame with a central passageway allowing the apparatus to slide along a cable or wire, frame, sensors, and/or samplers arranged so that their collective center of gravity lies below their collective centers of buoyancy and drag, and said centers of gravity, buoyancy and drag are approximately collinear with the central passageway, said frame, sensors, samplers and optional drag surfaces spatially arranged so that their weight and drag cause the frame to slide along the cable or wire stably at pre-determined rates, means to decelerate and stop the descending frame near the lower end of the wire or cable by dropping ballast or increasing buoyancy, whereupon the frame ascends by its buoyancy or by raising the cable.

3. The apparatus described in claim 1 or 2 wherein means allow attachment to and/or removal from a standing guide wire.

4. The apparatus described in claim 1 or 2 wherein means communicate with a surface or submerged vehicle using underwater acoustic telemetry, or communicate with the vehicle from which the guide wire is deployed through an inductive telemetry link.

5. A method for transporting equipment such as sensors and samplers at approximately constant velocity along a wire or cable, comprising the following steps:

mounting the equipment on a frame-like structure having a central passageway through which the guiding wire or cable passes;

arranging the equipment on the frame so that the collective center of gravity is below the collective centers of buoyancy and drag, and said centers of gravity, buoyancy, and drag are approximately collinear with the central passageway;

spatially arranging the equipment on the frame, optionally together with other drag elements, so to provide drag appropriate to achieving the desired decent velocity;

deploying the apparatus on a cable lowered into a body of water;

providing a deceleration device to stop the frame and equipment without damage at the lower end of the wire or cable;

retrieving the frame by raising the cable.

6. The method of claim 5 which includes attaching and/or removing the frame to a standing guide wire.

7. The method of claim 5 which includes communicating with a surface or submerged vehicle using underwater acoustic telemetry, or communicating with the vehicle from which the guide wire is deployed through an inductive telemetry link.

* * * * *